United States Patent [19]

Holtkamp, Sr.

[11] Patent Number: Plant 6,929

[45] Date of Patent: Jul. 18, 1989

[54] AFRICAN VIOLET PLANT NAMED LITTLE RUBY

[76] Inventor: Reinhold Holtkamp, Sr., Werther Strasse 112, D4294 Isselburg, Fed. Rep. of Germany

[21] Appl. No.: 192,679

[22] Filed: May 10, 1988

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of African violet named Little Ruby characterized by its miniature growth habit; single violet-shaped to semi-double red flowers; strong stems which curve toward the center to form a compact bouquet above the leaves; profuse and continuous flowering; dark green, spear-shaped leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha,* and hereinafter referred to by the cultivar name Little Ruby.

The new cultivar was referred to during the breeding and selection process by the designation I 463 and is a product of a planned breeding program. The new cultivar was originated from a cross made by me in the controlled breeding program in Haffen, Federal Republic of Germany. The female, or seed parent was a cultivar designated 4 Mini. The male, or pollen parent was a cultivar designated 69.

Little Ruby was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Little Ruby has not been observed under all possible environmental conditions. The phenotype may vary significantly with variations in environment such as temperature, light intensity and day length. The following observations, measurements and values describe the new cultivar as grown in a 4 cm pot in Haffen, West Germany and Nashville, Tenn. under greenhouse conditions which closely approximate those generally used in commercial practice.

The following traits have been repeatedly observed and are determined to be basic characteristics of Little Ruby, which in combination distinguish this African violet as a new and distinct cultivar:

(1) Little Ruby will not grow taller than 8 cm.
(2) Single to semi-double red flowers.
(3) Strong wirelike and upright flower stems curving toward the center.
(4) First flash of flowers form a tight bouquet above the leaves.
(5) Profuse flowering; under good growing conditions continuous flowering.
(6) Each plant carries 9–11 and more upright flower stems each of which carries 4 to 5 and more flowers.
(7) Long lasting, non-dropping flowers.

(8) Plant saleable 10 to 11 weeks after planting of unrooted shoot.
(9) Seed capsules push slightly through.
(10) Dark green, hairy leaves.
(11) Spear-shaped leaves are 2.0 to 3.0 cm in size.
(12) After maturity the flowers dry off, and remain on the peduncle.

The accompanying color photographic drawing shows a typical specimen plant of the new cultivar grown in a 4 cm pot. The plant is pictured on a hand to highlight the miniature size and growth habit of Little Ruby. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 2 p.m. in Nashville, Tenn.

Botanical classification: *Saintpaulia ionantha,* Ramat, c.v. Little Ruby.

Parentage:

*Male parent.*—69.

*Female parent.*—4 Mini.

Propagation: The new cultivar holds its distinguishing characteristics through successive propagations by leaf cuttings.

Plant: From 6 cm to 8 cm tall when grown in pots, and approximately 8–11 cm in diameter when fully grown.

*Leaves.*—General form: Spear-shaped. Diameter: 20–23 mm wide and 25–28 mm long. Texture: Leatherlike. Aspect: Shiny, hairy. Veins: Upperside: visible; underside: well pronounced, light green, shiny; on young leaves red. Color (upperside): Yellow-Green Group 147 between A and B. Color (underside): Yellow-Green Group 147 D, occasional touch of Red-Purple Group 49 between A and B. Young leaves are Red-Purple Group 49 between A and B before they turn green. Petiole: Strong, light green, occasionally purplish red touch, hairy.

*Flowers.*—Buds: Size: 3–4 mm just before opening. Shape: Bell-shaped. Color: Purplish green. Sepals: Five (5). Color: Purplish brown. Calyx: Shape: Funnel-shaped. Aspect: Spear-shaped, hairy. Peduncle: Character: Strong upright, hairy. Color: Purplish brown. Individual flowers: Size: 20–24 mm. Shape: Single violet-shaped to semi-double (up to six additional petals). Color (upperside): Red-Purple Group 72 between A and B. Under cooler temperatures and more intensive lighting, the red tends to intensify. Color (underside): Red-Purple Group 74 C. Borne: Each flower stem carries 4–5 and more flowers on strong, upright peduncle that are free standing above the leaves, thereby forming a compact bouquet. Flowering habit: Flowers 10–11 weeks after planting an unrooted plantlet.

*Reproductive organs.*—Stamens: Two (2). Anthers: 2 composed of 4 anther cells, seed capsule pushes slightly through. Filaments: Yellowish green with red touch, 2 mm long. Styles: 4 mm long, red, base of ovary light green and hairy.

*Roots.*—Normally developed, white when young, turning slightly brownish when older.

Disease resistance: Good.

General observations: Little Ruby is a super miniature violet, which does not grow taller than 8 cm. The red flowers are single violet-shaped to semi-double having up to 6 additional small petals. On semi-double blooms the anthers are sometimes covered up. The flowers are long-lasting and non-dropping. Under good growing conditions Little Ruby will bloom continuously. A nice bouquet of flowers free standing above the dark green, spear-shaped leaves develops approximately 10–11 weeks after planting an unrooted plantlet. Each of the 9–11 and more strong flower stems carries 4–5 and more flowers.

I claim:

1. A new and distinct cultivar of African violet named Little Ruby, as described and illustrated, and particularly characterized by its miniature growth habit; single violet-shaped to semi-double red flowers; strong stems which curve toward the center to form a compact bouquet above the leaves; profuse and continuous flowering; dark green, spear-shaped leaves; flowering 10–11 weeks after planting of unrooted shoot, and by its long lasting and non-dropping flowers.

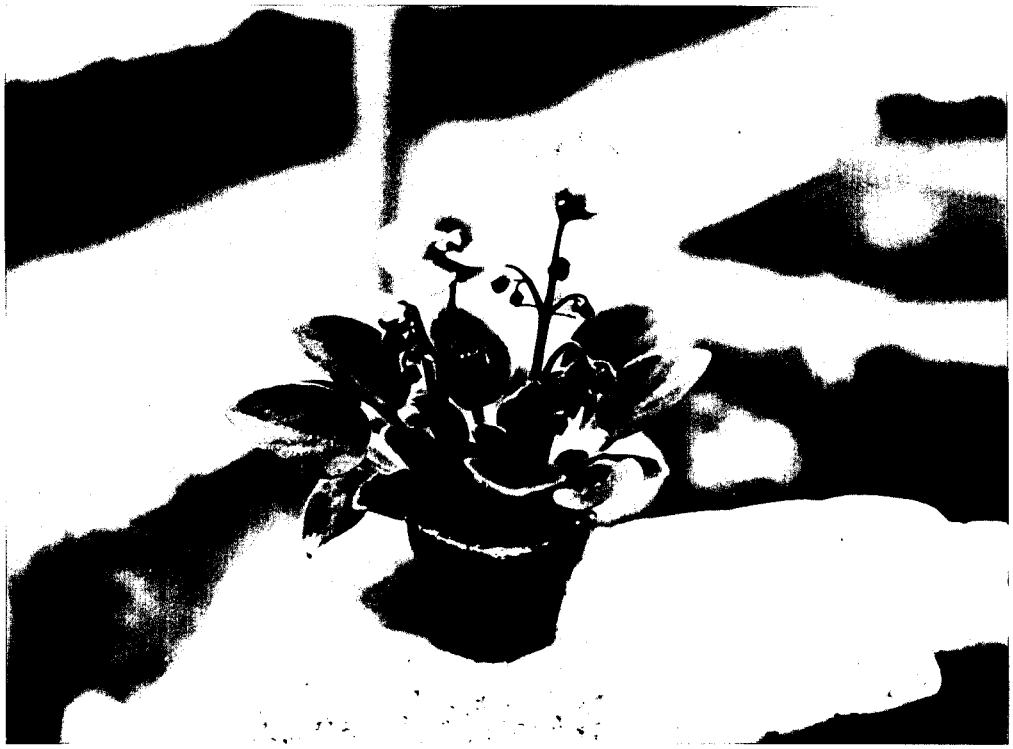

* * * * *